United States Patent [19]

Kojima et al.

[11] Patent Number: 4,690,932
[45] Date of Patent: Sep. 1, 1987

[54] COUMARINS WITH IMIDAZOLYL GROUP OR PYRIDYLOXY GROUP HAVING PLATELETES AGGREGATION INHIBITING ACTIVITY

[75] Inventors: Tadao Kojima, Saitama; Shunji Kageyama; Minoru Okada, both of Tokyo; Isao Ohata; Noboru Sato, both of Saitama, all of Japan

[73] Assignee: Yamanouchi Pharmaceutical Co., Ltd., Tokyo, Japan

[21] Appl. No.: 871,155

[22] Filed: May 30, 1986

Related U.S. Application Data

[63] Continuation of Ser. No. 626,283, Jun. 29, 1984, abandoned.

[30] Foreign Application Priority Data

Jul. 5, 1983 [JP] Japan .................................. 58-122222

[51] Int. Cl.[4] .................... C07D 405/12; A61K 31/44
[52] U.S. Cl. .................................. 514/337; 514/397; 546/269; 548/336

[58] Field of Search ................ 514/337, 397; 546/269; 548/336

[56] References Cited

PUBLICATIONS

Primufine et al., CA 88:37696Z.

Primary Examiner—Jane T. Fan
Attorney, Agent, or Firm—Burgess, Ryan & Wayne

[57] ABSTRACT

Novel coumarin compounds of the formula

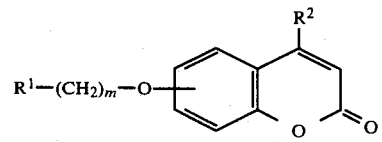

wherein $R^1$ represents an imidazolyl group or a pyridyloxy group which may be substituted by lower alkyl group(s); $R_2$ represents a hydrogen atom or a lower alkyl group; and m represents an integer of 1 to 6; and the salts thereof, which inhibit platelets aggregation.

18 Claims, No Drawings

COUMARINS WITH IMIDAZOLYL GROUP OR PYRIDYLOXY GROUP HAVING PLATELETES AGGREGATION INHIBITING ACTIVITY

This application is a continuation of application Ser. No. 626,283, filed June 29, 1984, now abandoned.

BACKGROUND OF THE INVENTION AND THE PRIOR ART

It is not known that coumarin derivatives have platelets aggregation inhibiting activity, until now.

DETAILED DESCRIPTION OF THE INVENTION

This invention relates to the novel coumarin compounds of the salts thereof shown by the formula (I)

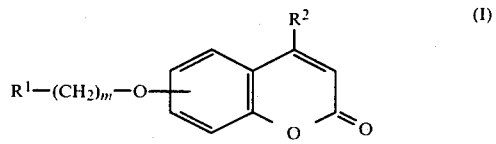

wherein $R^1$ represents an imidazolyl group or a pyridyloxy group which may be substituted by lower alkyl group(s); $R^2$ represents a hydrogen atom or a lower alkyl group, and m represents an integer of 1 to 6. $R^1$, $R^2$ and m hereunder have the same significances as above.

"Lower alkyl group" used in this invention includes straight chain- or branched chain-alkyl groups having from 1 to 5 carbon atoms, such as methyl group, ethyl group, propyl group, isopropyl group, butyl group, isobutyl group, sec-butyl group, tert-butyl group, pentyl group (amyl group), isopentyl group, neopentyl group, tert-pentyl group, etc.

Some typical compounds of this invention are as follows:

7-[5-(1-imidazolyl)pentyloxy]coumarin
7-[5-(6-methyl-3-pyridyloxy)pentyloxy]coumarin
7-[5-(3-pyridyloxy)pentyloxy]coumarin
7-[3-(1-imidazolyl)propoxy]coumarin
7-[5-(6-ethyl-3-pyridyloxy)pentyloxy]coumarin
7-[4-(6-methyl-3-pyridyloxy)butoxy]coumarin
7-[4-(1-imidazolyl)butoxy]coumarin
7-[3-(6-methyl-3-pyridyloxy)propoxy]coumarin
7-[5-(1-imidazolyl)ethoxy]-4-methylcoumarin
7-[(1-imidazolyl)methoxy]coumarin The compounds of this invention of the above formula (I) can form the salts thereof, and the salts include the pharmacologically acceptable salts of the compounds of this invention. As such salts, there are salts with an inorganic acid such as hydrochloric acid, sulfuric acid, hydrobromic acid, phosphoric acid, etc.; salts with an organic acid such as formic acid, acetic acid, lactic acid, oxalic acid, succninic acid, fumaric acid, maleic acid, methansulfonic acid, ethansulfonic acid, benzenesulfonic acid, etc.; and also the quaternary ammonium salts obtained by the reaction with an alkyl halide such as methyl iodide, etc.

The compounds of the formula (I) and the salts in this invention have platelets aggregation inhibiting activity which is particularly excellent, and are effective for the prophylaxis and the medical treatment for arteriosclerosis, cerebral embolism, cerebral embolism, cerebral infarction, transient paroxysmal ischemia, angina pectoris, peripheric thrombus and peripheric embolism.

The pharmacological effect of the compounds of this invention were examined in the following experiment.

Platelets aggregation inhibiting activity:

Platelet-rich plasma (PRP) and platelet-poor plasma (PPP) used for the experiment were obtained from Japan white rabbit's venous blood. Platelets aggregation rate and extent were determined in accordance with a method described in "Born, G. V. R.; Nature; 194, 927(1962)". For the platelets aggregation induced by arachidonic acid (final concentration: 0.3 mM), the effects of the compounds of this invention for inhibiting the platelets aggregation were measured by an instrumental meter sold on the market (the payton's aggregometer). As a result, it is clear that the compounds of this invention possess the inhibiting activity, and the effective concentration if $IC_{50}$: 10–100 $\mu M$.

The compounds of the formula (I) and the salts thereof in this invention can be formed into various pharmaceutical formulations such as powder, granule, tablet, capsule, injection, etc.; some additives for the formulations are generally used. The compounds can be administered orally (tablet, capsule, granule, powder, liquid, etc.) or parenterally (intravenous injection or intramuscular injection, suppository, etc.). The doses of the compounds depend upon the condition, age, etc. of the patient but in case or oral administration, the dose is usually 1–100 mg/kg, preferably about 5–25 mg/kg a day per an adult, and it is proper to administer the medicament (the compound of this invention) in 2 to 4 divided doses, or it may be administered in a single dose.

The compounds of the formula (I) in this invention can be prepared by various methods and, for example, can be prepared by the method shown below.

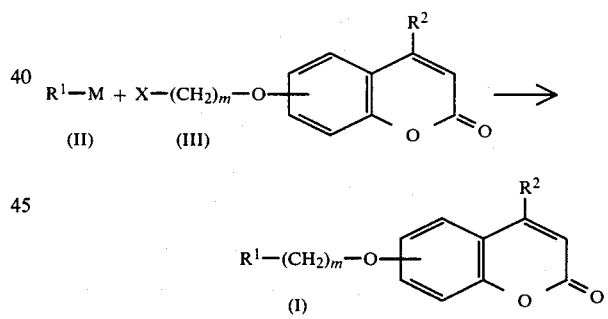

(In the above, M represents a hydrogen atom or alkali metal atom, X represents a halogen atom; and hereunder M and X have the same significance as above.)

Now, "halogen" for X includes chlorine, bromine, iodine, etc.; and "alkali metal" for M includes sodium, potassium, etc.

That is, the compound of the formula (I) in this invention can be prepared by reacting the imidazole compound or hydroxypyridine compound (M=H) shown by the formula (II) with the halogenoalkyloxycoumarin compound of the formula (III) in the presence of a base or a basic material. The compounds of the formula (I) in this invention can be prepared also by reacting the alkali metal salt of said imidazole compound or of said hydroxypyridine compound (M=alkali metal) with the compound of the formula (III).

It is preferred that the reaction (that is, N-alkylation or O-alkylation) is carried out at room temperature or under heating in an organic solvent such as alcohol (methanol, ethanol, etc.), dimethylsulfoxide, dimethylformamide, benzene, toluene, xylene, ether, tetrahydrofuran, etc.

The base or basic material for use in case of the direction reaction between imidazole or hydroxypyridine (II, M=H) and the compound (III) includes potassium carbonate, sodium hydroxide, sodium amide, alkali metal alcoholate such as sodium ethoxide, sodium hydride, etc., and organic lithium compound such as n-butyl lithium, etc.

Other than the above-mentioned preparation method, there are various methods for preparing the compounds of this invention.

For example, the compounds of this invention can be prepared by reacting the halogenoalkyl imidazole or halogenoalkoxy pyridine of the formula (IV)

R$^1$—(CH$_2$)$_m$—X with the hydroxycoumarin compound (or the alkali metal salt thereof) of the formula (V)

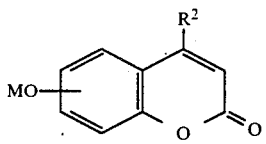

in the similar manner as above.

The compounds of this invention prepared as above are isolated and purified as the free compounds or the salts thereof.

The isolation or purification is conducted by a conventional chemical operation usually used in the field of the art, such as recrystallization, extraction, distillation, concentration, various chromatographies, and crystallization, etc.

Hereafter the present invention will be described in more detail with reference to the examples. Some of the starting compounds of the present invention are novel and preparation of such compounds is shown in the reference examples. The compounds of the reference examples serve for the reaction as the compound (III).

REFERENCE EXAMPLE

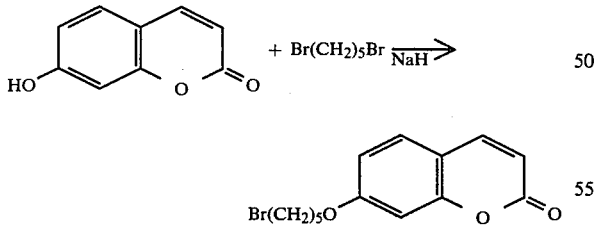

After 4.0 g of sodium hydride (60% suspension in a mineral oil) was washed with dry benzene, 100 ml of dry dimethylformamide was added thereto. While stirring at room temperature, 16.2 g of 7-hydroxycoumarin was added to the mixture. After vigorous bubbling was over, the resulting suspension was heated at 80° C. for 30 minutes while stirring and then cooled to room temperature. A solution of 15 ml of 1,5-dibromopentane in 30 ml of dry N,N'-dimethylformamide was added thereto. And, heating was conducted at 60° C. for 4 hours while stirring. The solvent was removed from the reaction liquid by distillation under reduced pressure. The residue was dissolved in methylene chloride and the solution was successively washed with a 5% aqueous sodium hydrogen carbonate solution, water and then a saturated aqueous sodium chloride solution followed by drying over anhydrous sodium sulfate. After drying over anyhydrous sodium sulfate, the solvent was distilled off under reduced pressure. The oily residual was subjected to silica gel column chromatography and the desired product was eluted using a benzene:n-hexane mixture (1:5) as an eluant. The solvent was removed from the eluate by distillation under reduced pressure to obtain the desired compound, 7-(5-bromopentyloxy)-coumarin, as an oily substance.

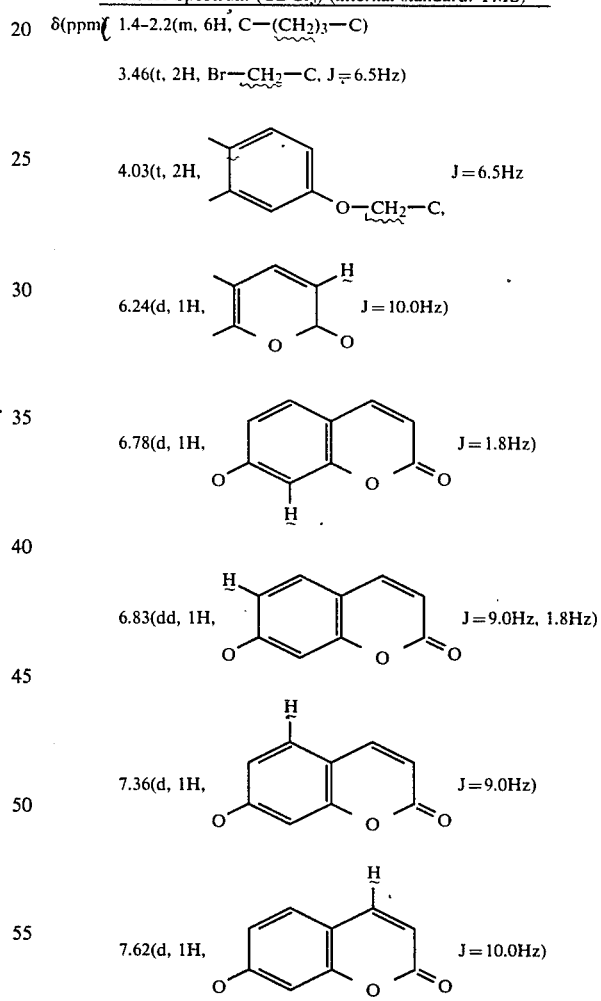

EXAMPLE 1

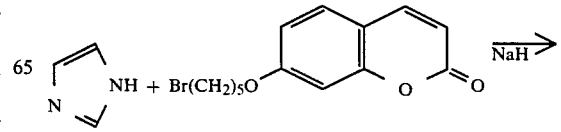

-continued

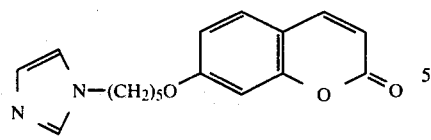

After 0.4 g of sodium hydride (60% suspension in a mineral oil) was washed with dry benzene, 30 ml of dry N,N'-dimethylformamide was added thereto. While stirring at room temperature, 0.7 g of imidazole was added to the mixture. After vigorous bubbling was over, the resulting suspension was heated at 80° C. for 30 minutes while stirring and then cooled to room temperature. A solution of 3.1 g of 7-(5-bromopentyloxy)-coumarin in 10 ml of dry N,N-dimethylformamide was added thereto. And, heating was conducted at 60° C. for 4 hours while stirring. The solvent was removed from the reaction liquid by distillation under reduced pressure. The residue was dissolved in methylene chloride and the solution was successively washed with a 5% aqueous sodium hydrogen carbonate solution, water and then a saturated aqueous soidum chloride solution followed by drying over anhydrous sodium sulfate. After drying, the solvent was distilled off under reduced pressure. The residual oily substance was subjected to silica gel column choromatography and the desired product was eluted using a chloroform:methanol (99:1) as an eluant. The solvent was removed from the eluate by distillation under reduced pressure to obtain the desired compound, 7-[5-(1-imidazolyl)pentyloxy]coumarin as an oily substance. The hydrochloride salt of this compound has a melting point of 134°-135° C. after recrystallization from ethanol.

| Elemental Analysis (as $C_{17}H_{19}N_2O_3Cl$) | | | | |
|---|---|---|---|---|
| | C(%) | H(%) | N(%) | Cl(%) |
| Calculated: | 60.99 | 5.72 | 8.37 | 10.59 |
| Found: | 60.73 | 5.88 | 8.36 | 10.30 |

EXAMPLE 2

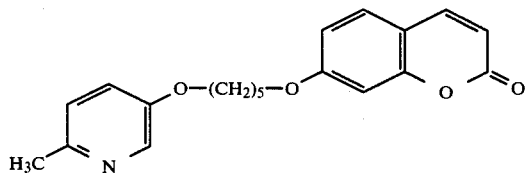

In accordance with the same procedure as in Example 1, using 6-methyl-3-hydroxypyridine instead of imidazole, 7-[5-(6-methyl-3-pyridyloxy)pentyloxy]coumarin was obtained after recrystallization from ethyl acetate. Melting point: 101°-102° C.

| Elemental Analysis (as $C_{20}H_{21}NO_4$) | | | |
|---|---|---|---|
| | C(%) | H(%) | N(%) |
| Calculated: | 70.78 | 6.24 | 4.13 |
| Found: | 70.51 | 6.35 | 4.09 |

EXAMPLE 3

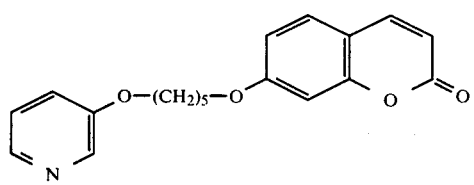

In accordance with the same procedure as in Example 1, using 3-hydroxypyridine instead of imidazole, 7-[5-(3-pyridyloxy)pentyloxy]coumarin (desired compound) was obtained after recrystallization from ethyl acetate. Melting point: 88°-89° C.

| Elemental Analysis (as $C_{19}H_{19}NO_4$) | | | |
|---|---|---|---|
| | C(%) | H(%) | N(%) |
| Calculated: | 70.14 | 5.89 | 4.30 |
| Found: | 70.03 | 5.83 | 4.30 |

We claim:
1. A coumarin compound of the formula

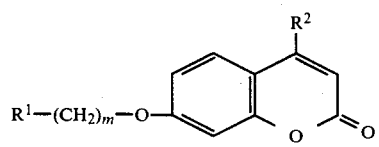

wherein $R^1$ represents an imidazolyl group or a pyridyloxy group which may be substituted by lower alkyl group(s) of from 1 to 5 carbon atoms; $R^2$ represents a hydrogen atom or a lower alkyl group; and m represents an integer of 1 to 6; or a pharmacologically acceptable salt thereof.

2. A compound as claimed in claim 1 wherein said lower alkyl group contains from 1 to 5 carbon atoms.

3. A compound as claimed in claim 1 wherein said lower alkyl group is methyl or ethyl.

4. A compound as claimed in claim 1 wherein said $R^1$ represents imidazolyl.

5. A compound as claimed in claim 1 wherein said $R^1$ represents pyridyloxy.

6. A compound as claimed in claim 1 wherein said $R^1$ represents 3-pyridyloxy.

7. A compound as claimed in claim 1 which is 7-[5-(1-imidazolyl)pentyloxy]coumarin.

8. A compound as claimed in claim 1 which is 7-[5-(3-pyridyloxy)pentyloxy]coumarin.

9. A compound as claimed in claim 1 which is 7-[5-(6-methyl-3-pyridyloxy)pentyloxy]coumarin.

10. A compound as claimed in claim 1 which is 7-[5-(3-pyridyloxy)pentyloxy]coumarin hydrochloride.

11. A compound as claimed in claim 2 wherein said pyridyloxy is 3-pyridyloxy substitutable by lower alkyl.

12. A compound as claimed in claim 2 wherein said imidazolyl is 1-imidazolyl.

13. A compound as claimed in claim 2 wherein said lower alkyl is methyl, ethyl, propyl, iso-propyl, butyl, iso-butyl or pentyl.

14. A compound as claimed in claim 1 wherein said salts are inorganic acid addition salts and organic acid addition salts.

15. A salt of the compound claimed in claim 1 which is hydrochloride.

16. A pharmaceutical composition having platelet aggregation inhibiting activity which comprises an effective inhibiting amount of a compound or the salt thereof as claimed in claim 1, and a pharmaceutically acceptable carrier.

17. A method for inhibiting the aggregation of platelets in a host which comprises administering to said host a pharmaceutically effective amount of the composition of claim 16.

18. The method of claim 17 wherein said composition is administered in a dose range of from 1 to 100 milligrams per kilogram.

* * * * *